(12) United States Patent
Dickie

(10) Patent No.: US 12,357,275 B2
(45) Date of Patent: Jul. 15, 2025

(54) ULTRASOUND SYSTEMS AND METHODS FOR USER INTERFACE ON IMAGE TOUCHSCREEN CONTROL OF FOCAL ZONE ADJUSTMENTS

(71) Applicant: Clarius Mobile Health Corp., Vancouver (CA)

(72) Inventor: Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 193 days.

(21) Appl. No.: 17/967,302

(22) Filed: Oct. 17, 2022

(65) Prior Publication Data
US 2024/0122573 A1 Apr. 18, 2024

(51) Int. Cl.
*A61B 8/00* (2006.01)
*A61B 8/08* (2006.01)
*G01S 15/89* (2006.01)

(52) U.S. Cl.
CPC .............. *A61B 8/463* (2013.01); *A61B 8/085* (2013.01); *A61B 8/5207* (2013.01); *G01S 15/899* (2013.01); *G06T 2207/10132* (2013.01)

(58) Field of Classification Search
CPC ....... A61B 8/463; A61B 8/085; A61B 8/5207; A61B 8/468; A61B 8/48; A61B 8/12;
(Continued)

(56) References Cited

U.S. PATENT DOCUMENTS 7,274,325 B2 * 9/2007 Fattah ................. G01S 7/52044
600/407
10,420,533 B2 9/2019 Kim et al.
(Continued)

FOREIGN PATENT DOCUMENTS

KR 102190028 B1 12/2020

OTHER PUBLICATIONS

E-Echocardiography. 2000-2022 JLS Interactive, LLC. "Ultrasound Beam Shape & Focusing", publication date unknown, available online: https://e-echocardiography.com/page/page.php?UID=1429454181, last accessed Nov. 22, 2022.

*Primary Examiner* — Keith M Raymond
*Assistant Examiner* — Patrick M Mehl
(74) *Attorney, Agent, or Firm* — Julian Ho; Susan Ben-Oliel

(57) ABSTRACT

The present embodiments relate generally to ultrasound imaging systems and methods that provide, upon receipt of input of a tap gesture at a location directly on the ultrasound image feed on the touchscreen display, such location indicating on the post scan converted ultrasound image frame a desired focal adjustment point, the processor causes the ultrasound imaging system to i) revert the post scan converted ultrasound image frame comprising the location of the desired focal adjustment point, by way of the cartesian co-ordinates, to its corresponding pre-scan raw ultrasound data frame; ii) calculate, on the pre-scan raw ultrasound data frame, the location of the desired focal adjustment point, by way of polar co-ordinates of the desired focal adjustment point; and iii) adjust at least one beamformer parameter of ultrasound signals being used to transmit and receive the ultrasound image to focus at the desired focal adjustment point, based upon the polar coordinates.

20 Claims, 11 Drawing Sheets

(58) Field of Classification Search
CPC ......... A61B 8/461; A61B 8/465; A61B 8/467; A61B 8/469; A61B 8/54; G01S 15/899; G01S 7/52047; G01S 7/52073; G01S 7/5208; G01S 7/52084; G06T 2207/10132
See application file for complete search history.

(56) References Cited

U.S. PATENT DOCUMENTS

| | | | |
|---|---|---|---|
| 2007/0016022 A1* | 1/2007 | Blalock | A61B 8/4488 |
| | | | 600/437 |
| 2010/0049046 A1 | 2/2010 | Peiffer et al. | |
| 2014/0098049 A1* | 4/2014 | Koch | A61B 8/461 |
| | | | 345/173 |
| 2014/0323872 A1 | 10/2014 | Eom et al. | |
| 2018/0220995 A1 | 8/2018 | Pelissier et al. | |
| 2020/0330076 A1* | 10/2020 | Weber | G01S 7/52033 |
| 2020/0337678 A1 | 10/2020 | Hansen et al. | |

* cited by examiner

ULTRASOUND SYSTEMS AND METHODS FOR USER INTERFACE ON IMAGE TOUCHSCREEN CONTROL OF FOCAL ZONE ADJUSTMENTS

FIELD

The present disclosure relates generally to ultrasound imaging, and in particular, user interface controls for modifying imaging parameters on ultrasound systems.

BACKGROUND

Ultrasound imaging systems are a powerful tool for performing real-time, non-invasive imaging procedures in a wide range of medical applications. An ultrasound machine includes a transducer which sends out ultrasound signals into tissue. Ultrasound waves are reflected back from the tissue and are received by the transducer. The reflected signals are processed to produce an ultrasound image of the target anatomy. An ultrasound machine typically has a user input device by which the operator of the ultrasound machine can control the machine to obtain images of tissue structures. Traditionally, the images may be displayed on a display incorporated in the ultrasound machine, and the user input device may include a keyboard.

A challenging part of acquiring ultrasound images is adjusting the various imaging parameters to optimize the image viewable. Conventional ultrasound systems have large physical control interfaces with numerous controls that allow modifying of various imaging parameters affecting the displayed image quality. It is typically required that multiple controls need to be manipulated to achieve an image with good quality. The manipulation of multiple controls to optimize image quality may not be intuitive, and users may require extensive training to learn the how the operation of these controls impact image quality.

In addition, there is an increasing demand for small portable ultrasound imaging devices (point of care ultrasound systems or POCUS) that are easier to operate and that acquire good quality ultrasound images of the target anatomy. Small portable devices typically have smaller screens, and thus less room to display the many user interface controls traditionally appearing on an ultrasound user interface. On some existing ultrasound systems that provide ultrasound images on a touchscreen display, on-screen controls mimic the physical controls of a traditional ultrasound imaging system. These types of controls may obscure viewing of the ultrasound images being acquired and as such may not provide a way to adjust imaging parameters in a manner that easily allows the imaging parameters to be previewed prior to adjustment.

Even more specifically, there is a need to properly and accurately control and adjust very specific focal zones while imaging. Typically, focal zones are managed through a knob/dial or switch on the console of cart-based systems, or on some touchscreen systems, and adjustment would require either dragging an arrow along the edge of the ultrasound image or sliding screen buttons up and down. On any and all of these systems, there are accuracy and time-delay issues in pinpointing and then updating a desired new focal point. Furthermore, POCUS commonly employs a user interface of a multi-purpose electronic device (such as, for example an iPAD®) to control and operate a transducer (including setting adjustments) and such a screen offers less space for accurate use of sliding and dragging motions to direct focal point adjustments.

As such, there is thus a need for improved ultrasound systems and methods that optimize focal point/zone adjustments. The embodiments discussed herein address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

A. Glossary

Figure 1:
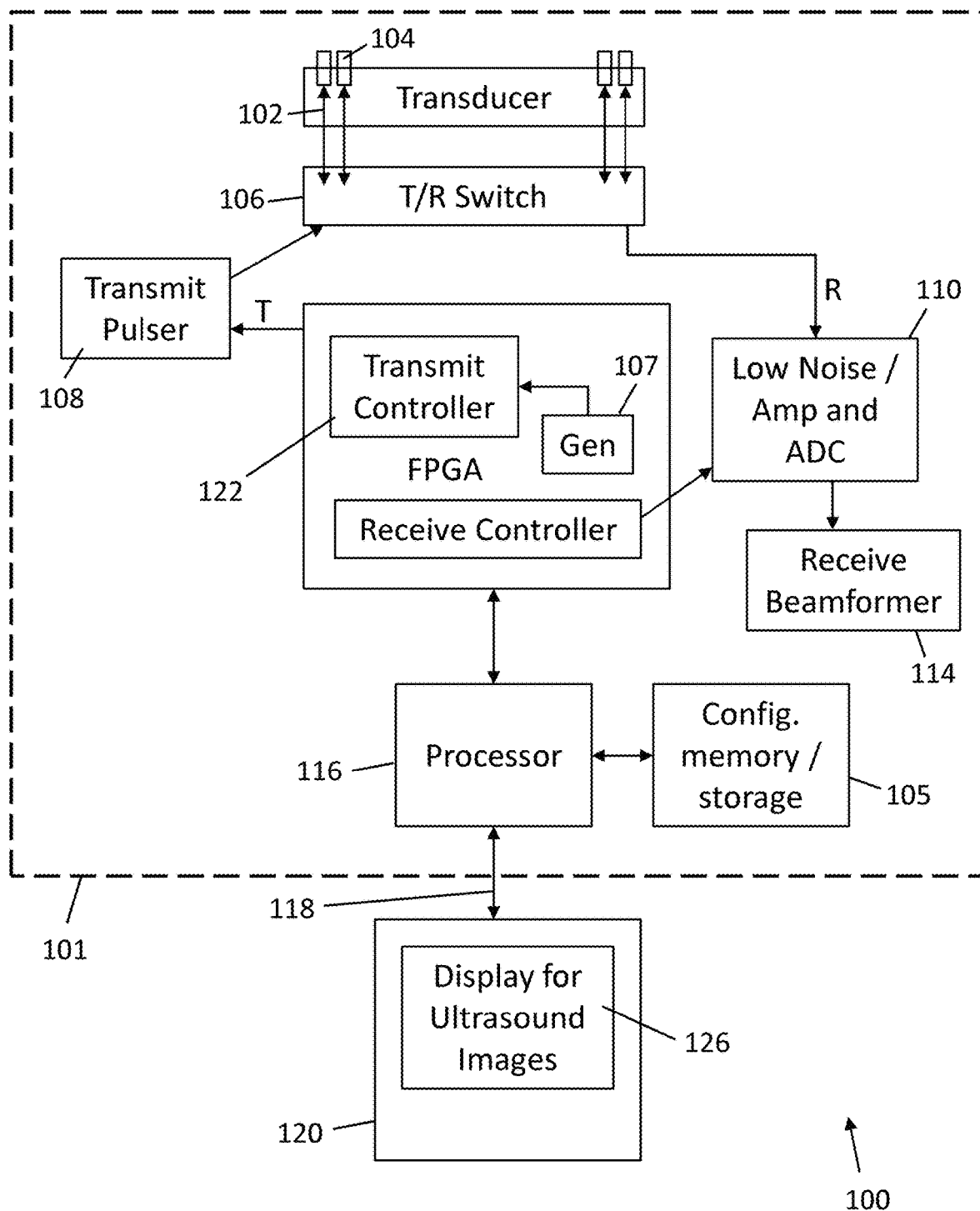
FIG. 1 shows a functional block diagram of a handheld or hand-carried medical ultrasound machine according to certain embodiments of the present disclosure.

The term "anatomical feature" means any part of a human body, an animal, or phantom, and may refer to an entire organ, a part of an organ, damage to an organ, abnormality of an organ, illness, an unwanted growth, and the like. In obstetric practise, it may refer to an entire fetus, part of a fetus, or an entire organ, a part of an organ, damage to an organ, abnormality of an organ, illness, an unwanted growth, and the like.

The term "back converting" also, back conversion or back convert or any of its grammatical forms, means to perform a reverse scan conversion, which is to convert an ultrasound image back to its corresponding raw ultrasound data frame, or to a raw ultrasound data frame in a standardized format. The standardized format may be defined, for example, by a fixed number of scan lines and a fixed number of samples in each scan line. Back converting may also apply to markings made on an ultrasound image, which may delineate an anatomical feature, in which case the coordinates of the markings are transformed from the coordinate system of the ultrasound image to the coordinate system of the raw ultrasound data frame. The back converting of markings and their insertion, combination or association with a raw ultrasound data frame may be considered to be an interpolation of the markings into the raw ultrasound data frame.

The term "beam focusing" refers to a method of creating a narrow point in the cross-section of the ultrasound beam called the focal point. It is at the focal point where the lateral resolution of the beam is the greatest also. Before the focal point is the near field or Fresnel zone, where beams converge and distal to this focal point is the far field or Fraunhofer zone where the beams diverge.

The term "cartesian coordinate" or "cartesian coordinate system in a plane" is an x-y coordinate system that specifies each point uniquely by a pair of numerical coordinates, which are the signed distances to the point from two fixed perpendicular oriented lines, measured in the same unit of length. Each reference coordinate line is called a coordinate axis or just axis (plural axes) of the system, and the point where they meet is its origin, at ordered pair (0, 0). The coordinates can also be defined as the positions of the perpendicular projections of the point onto the two axes, expressed as signed distances from the origin.

The term "communications network" and "network" can include both a mobile network and data network without limiting the term's meaning, and includes the use of wireless (e.g. 2G, 3G, 4G, 5G, WiFi, WiMAX®, Wireless USB (Universal Serial Bus), Zigbee®, Bluetooth® and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "coordinate converting" or any of its grammatical forms, refers to the conversion of data from polar coordinates to cartesian coordinates (scan conversion as define below) or cartesian coordinates to polar coordinates (back converting as defined above). Ultrasound scanners gather data in the form of polar coordinates whereas conventional display interfaces, such as for example those on multi-purpose electronic devices, comprise a rectangular grid, and this grid configuration requires the use of cartesian coordinates to enable display of images thereon.

The term "depth" when relating to an ultrasound image refers to a measure of how far into the anatomical feature or structure being scanned (e.g., tissue or a phantom) a given ultrasound image shows.

The term to "focal point" refers to a specific area of desired image optimization and when focus or focal point is adjusted, this simply concentrates ultrasound waves at a specific depth of the image to maximize the resolution at that depth. Some ultrasound transducers do not allow for user adjusted focusing instead relying upon an auto-focusing feature. If an ultrasound transducer does enable user directed focus selections, this is achieved in known, conventional ultrasound systems by using a depth adjustment tool on the user interface or knob controls on a console. Usually, the focus is indicated by a small arrow (or hourglass) superimposed on the vertical depth markings.

The term "interpolating" means to back convert markings or their coordinates, which may delineate an anatomical feature on an ultrasound image, from the coordinate system of the ultrasound image to the coordinate system of a raw ultrasound data frame and insert, combine or otherwise associate them with the raw ultrasound data frame.

The term "module" can refer to any component in this invention and to any or all of the features of the invention without limitation. A module may be a software, firmware or hardware module, and may be located, for example, in the ultrasound scanner, a display device or a server.

The term "multi-purpose electronic device" is intended to have broad meaning and includes devices with a processor communicatively operable with a screen interface, for example, such as, smartphones, tablets and portable computers.

The term "operator" (or "user") may (without limitation) refer to the person that is operating an ultrasound scanner (e.g., a clinician, medical personnel, a sonographer, ultrasound student, ultrasonographer and/or ultrasound technician).

The term "polar coordinate" or "polar coordinate system" is an coordinate system that refers to a two-dimensional (R, theta) coordinate system in which each point on a plane is determined by a distance from a reference point and an angle from a reference direction. The reference point (analogous to the origin of the cartesian coordinate system) is called the pole, and the ray from the pole in the reference direction is the polar axis. The distance from the pole is called the radial coordinate, radial distance or simply radius (abbreviated R), and the angle is called the angular coordinate, polar angle, or azimuth (theta). Angles in polar notation are generally expressed in either degrees or radians, with $2\pi c$ rad being equal to 360°.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "raw ultrasound data" or "raw ultrasound data frame" means a frame of lines of ultrasound scan data representing echoes of ultrasound signals acquired by an ultrasound scanner. The data is organized or stored using raw data (polar) coordinates, which is a typical form of the data prior to being scan converted.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates. In other words, this conversion is from a polar to a cartesian space, producing the rasterization of vector data onto a discrete cartesian grid using interpolation and scaling.

The term "system" when used herein, and not otherwise qualified, refers to a system for enabling an automatic focal point adjustment based upon a simple tap gesture from a user at a location directly on an ultrasound image feed on a touchscreen display, such location indicating, on a post scan converted ultrasound image frame, a desired focal adjustment point, the system being a subject of the present invention. In various embodiments, the system may include an ultrasound machine (including a display and one or more transducers); an ultrasound scanner and a display device; and/or an ultrasound scanner, display device and a server.

The term "ultrasound image frame" (or "image frame" or "ultrasound frame") refers to a frame of post-scan conversion data that is suitable for rendering an ultrasound image on a screen or other display device.

The term "ultrasound transducer" (or "probe" or "ultrasound probe" or "transducer" or "ultrasound scanner" or "scanner") refers to a wide variety of transducer types including but not limited to curved transducers, curvilinear transducers, convex transducers, microconvex transducers, endocavity probes, and including any probes with smaller footprints and a tighter radius of curvatures. For greater clarity, within the scope of the present disclosure, when the term "curvilinear" is used within preferred aspects of the invention, it is intended to include a wider variety of non-linear transducer options. For even greater clarity, the method and system of the invention can be also used on linear transducers.

B. Exemplary Embodiments

The system and method of the present invention uses a transducer (a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

At a high level, the embodiments herein allow for the provision of ultrasound systems and ultrasound-based methods to adjust one or more focal points directly on a post-scan converted ultrasound image frame to assist in enhanced desired viewing of a feature or zone, feature selection, diagnosis and treatment, as and if required. The method and system of the present invention are particularly although not exclusively useful wherein an image capture on a touchscreen display shows a curvilinear ultrasound image feed, and a tap gesture on the touchscreen is at a location on or near an outer edge of the curvilinear ultrasound image feed. This is due to the unique view of such a curvilinear feed. A curvilinear ultrasound transducer (probe) provides a broader view that could be obtained via a smaller acoustic window and the ultrasound image of deeper structures is wider than the actual footprint of the probe. This factor of widening of the ultrasound image with the depth must be accounted for during distance measurement and has made, in the art and known focal point adjustment methods prior to the present invention, determining the precise depth of a scanned feature/structure (including focal point determination and adjustment) and width assessment with a curvilinear probe highly challenging. It is necessary to understand that the width of an ultrasound image created by a curvilinear probe is equal to the probe footprint size only at the uppermost part of the ultrasound image, and the depth marks on the side of the touchscreen are pertinent only for measurement of the depth on the line drawn through the middle or centre line of the probe. This is explained in further detail, along with practical implications, with reference to FIGS. 4-8.

Ultrasound transducers use two main techniques to focus an ultrasound image on a desired focal point: 1) transmit focusing and 2) dynamic focusing. Transmit focusing occurs by adding a time delay to the firing of each of the piezoelectric elements wherein the outermost elements are fired first with the center-most element fired last. The ultrasound pulses constructively interact to create a composite pulse which converges at the focal point and the focal depth is determined by the time delay between these pulses. Greater focal depths are achieved by reducing the difference in the time delay between the elements resulting in more beam divergence and greater depths and hallower focal depths increase the difference in the time delay between the elements.

In contrast, dynamic receiving focusing echoes received at the outer most elements of the array travel a longer distance than those at the center of the array hence re-phasing is needed to prevent a loss of resolution. Dynamic receiving focusing re-phases the signal by introducing electronic delays as a function of depth wherein a smaller time delay is needed for echoes returning from a greater depth and a larger time delay is needed for echoes returning from a shallower depth.

In a first broad aspect of the present disclosure, there is provided an ultrasound imaging system, including a touchscreen display; and a processor configured to execute instructions that cause the processor to provide a user interface on the touchscreen display, the user interface comprising an ultrasound image feed comprising a post scan converted ultrasound image frame; wherein upon receipt of input of a tap gesture at a location directly on the ultrasound image feed on the touchscreen display, such location indicating on the post scan converted ultrasound image frame a desired focal adjustment point, the processor causes the ultrasound imaging system to revert the post scan converted ultrasound image frame comprising the location of the desired focal adjustment point, by way of the cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image to focus at the desired focal adjustment point, based upon the polar coordinates.

In another broad aspect of the present disclosure, there is provided a method for adjusting a focal point on an ultrasound image feed, acquired from an ultrasound transducer, the method comprising providing a touchscreen display on a multi-purpose electronic device, the touchscreen display showing the ultrasound image feed comprising a post scan converted ultrasound image frame; receiving a tap gesture at a location directly on the post scan converted ultrasound image frame on the touchscreen display, such location indicating a desired focal adjustment point, to modify the imaging depth of the ultrasound image feed; upon receipt of the tap gesture, revert the post scan converted ultrasound image frame comprising the location of the desired focal adjustment point, by way of cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image frame to focus at the desired focal adjustment point, based upon the polar coordinates.

In another broad aspect of the present disclosure, there is provided a, computer readable medium storing instruction for execution by a processor communicatively coupled with a touchscreen display for an ultrasound imaging system, wherein when the instructions are executed by the processor, it is configured to show a touchscreen display on a multi-purpose electronic device, the touchscreen display comprising an ultrasound image feed with a post scan converted ultrasound image frame; receive a tap gesture at a location directly on the post scan converted ultrasound image frame on the touchscreen display, such location indicating a desired focal adjustment point, to modify the imaging depth of the ultrasound image feed; upon receipt of the tap gesture, revert the post scan converted ultrasound image frame comprising the location of the desired focal adjustment point, by way of cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image frame to focus at the desired focal adjustment point, based upon the polar coordinates.

The present invention provides, in another aspect a touchscreen display, comprising an interface responsive to a tap gesture thereon and communicatively associated with a processor, wherein the processor is configured to execute instructions that cause the interface on the touchscreen display to show an ultrasound image feed comprising post scan converted ultrasound image frame; wherein upon receipt of input of the tap gesture at a location directly on the ultrasound image feed on the touchscreen display, such location indicating on the post scan converted ultrasound image frame a desired focal adjustment point, the processor causes the ultrasound imaging system to revert the post scan converted ultrasound image frame comprising the location of the desired focal adjustment point, by way of the cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image to focus at the desired focal adjustment point, based upon the polar coordinates.

For simplicity and clarity of illustration, where considered appropriate, reference numerals may be repeated among the figures to indicate corresponding or analogous elements or steps. Various ultrasound images are shown in the drawings are not drawn to scale and are provided for illustrative purposes in conjunction with the description. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures, and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, which illustrates one embodiments of an ultrasound imaging system (generally shown as 100) and comprising an ultrasound machine (also referred to herein as an ultrasound scanner) 101 with a beamforming architecture in accordance with some embodiments of the present invention. Machine 101 includes a transducer array 102 that comprises a plurality of transducer elements 104. Transducer elements 104 are operable to both emit and receive ultrasound energy. When energized by a transmitter (transmit pulser) 108, the transducer elements 104 produce a burst of ultrasonic energy. To conserve space, power, and cost, often only a subset of transducer elements 104 are active for a particular transmit event. This subset of elements forms a transmit aperture.

The ultrasound energy produced by transducer array 102 is directed toward a body region of a patient containing a region of interest. Some of the ultrasound energy is then reflected back to transducer array 102 as echo signals. Again, to conserve space, power, and cost, often a subset of transducer elements is used to receive the echo signals; this subset of elements form the receive aperture. The transducer elements 104 in the receive aperture convert the received ultrasound energy into analog electrical signals which are then sent through a set of transmit/receive (T/R) switches 106 to yield channels of echo data. The transmission switches may include a high-voltage multiplexer. A set of analog-to-digital converters (ADCs) 110 digitises the analog signals from the switches. The digitised signals are then sent to a receive beamformer 114.

Transmitter 108 is operated under the control of a transmit controller 122. The ultrasound machine generates and processes additional transmit and receive events to produce the multiple scanlines required to form an image. Ultrasound images are typically made up of 50 to a few hundred lines. Lateral resolution can be improved by increasing the number of lines in each image. However, increasing the number of lines tends to reduce the achievable frame rate. It is not mandatory that the scanlines and/or transmit beams originate at the center of the transducer. For example, where the transducer comprises a linear array or curved array of transducer elements, receive apertures and delays may be selected such that scanlines are parallel to one another. For example, all or a number of the scanlines may be parallel to the transmit beam.

The transmit beamformer is configured to generate transmission signal and add a delay time to the transmission signals and thereby form a transmission signal pattern, and the transmit pulser is configured to generate the transmission pulse configured to drive the transducer elements (constituting the transducer array) according to the desired transmission signal pattern. The transmit pulser 108 applies transmission pulses to the transducer array so as to cause the transducer array to transmit ultrasound signals to a target region (region of interest) inside a subject. Further, the transmission beam former forms a transmission signal pattern on the basis of the time delay value which the transmit controller 122 calculates for each of the ultrasound transducer elements constituting the two-dimensional ultrasound transducer array (104) and transmits the formed transmission signal pattern to the transmit pulser 108. Data link 118 may generally comprise a cable or more preferably a wireless connection, or the like, enabling multipurpose electronic device 120, comprising user display/interface screen 126: i) to communicatively connect with the ultrasound machine 101; ii) to send and receive signals and data to/from ultrasound machine 101; and iii) to display an ultrasound image to a user via user display/interface screen 126.

Ultrasound machine 101 may be handheld or hand carried. Ultrasound machine 101 may comprise a time-shared beamforming coefficient generator 107 which dynamically calculates delay or delay and weight values for each channel. The delay and weight values for each channel are based on the origin and direction of the beam, the speed of propagation of the beam in the tissue, and the location of the transmit element corresponding to the channel relative to the beam. Examples of these calculations are described in more detail below, in the context of calculating, using a new depth of a new focal point, a new transmit focal point/aperture ("transmit beamformer").

The delay and weight values are communicated via a beamforming coefficient bus 1 to a plurality of beamformers. The beamformed data produced by each beamformer may be further processed in a manner similar to that in other typical ultrasound machines. Beamformers within the scope of the invention may be implemented in a programmable logic device, such as a field programmable gate array (FPGA). Configuration information such as, but not limited to, the number of beamformers and the number of channels, may be stored in a configuration memory 105 in communication with transmit controller 122. The number of beamformers may be predetermined and constant, or variable. For example, the number of beamformers could be changed by the user and/or changed automatically in response to a signal such as power level.

Alternatively, beamformers within the scope of the invention could be implemented on an application specific integrated circuit (ASIC). Since the beamformer does not include the complexity of the delay and weight calculators, a suitable beamformer may comprise only simple logic and a small amount of memory, requiring limited logic resources. Since fewer logic resources are required for each beamformer, the system is scalable to a larger number of beamformers than might otherwise be practical.

In embodiments where beamformers are provided by configuring an FPGA or other configurable logic device, it is only necessary to configure the logic device to provide a desired number of beamformers. For example, different configurations of the logic device may provide 2, 4, 8 or 16 beamformers (note the number of beamformers is not limited to powers of two, these are just convenient examples). The configurable logic device may also be configured to provide connections of the beamformer coefficient bus to each of the beamformers.

In embodiments where beamformers are provided in ASICs or other hard-wired configurations, the number of beamformers that are active may be varied. Non-active beamformers may be shut off or run in a standby mode to save power. In such embodiments, when the number of active beamformers is changed the operation of the beamformer coefficient generator may also be changed such that beamformer coefficients are generated and/or distributed only for the ones of the beamformers that are currently active.

Although not illustrated, the ultrasound imaging system 100 may include other components for acquiring, processing and/or displaying ultrasound image data. These include, but are not limited to: a scan generator, signal processor, data compressor, wireless transceiver and/or image processor. Each of these (and other) components may form part of ultrasound machine 101 and/or multipurpose electronic device 120, comprising interface screen 126.

Ultrasound imaging system 100 may include multipurpose electronic device 120 which is in communication with ultrasound machine 101 via data link 118. In various embodiments, data link 118 may allow for wired or wireless connectivity (e.g., via Wi-Fi™ and/or Bluetooth™) between the multipurpose electronic device 120 and the ultrasound machine 101. Multipurpose electronic device 120 may work in conjunction with ultrasound machine 101 to control the operation of ultrasound machine 101 and display the images acquired by the ultrasound machine 101. An ultrasound operator may interact with interface screen 126 to send control commands to the ultrasound machine 101 to control general operation of the image acquisitions, image manipulations and image adjustments, including a tap gesture to adjust focal point, as described herein.

Interface/display screen 126 comprises a display screen, which displays images based on image data acquired by ultrasound machine 101. More particularly, interface screen 126 comprises a touch interface layered on top of the display screen. Multipurpose electronic device 120 may also include memory, Random Access Memory (RAM), Read Only Memory (ROM), and persistent storage device, which may all be connected to a bus to allow for communication therebetween and with one/more processors. Ultrasound machine 101 may contain memory (e.g., storage devices) such as 105 that may be accessible by processor 116 and processor 1154. Any number of these memory elements may store software or firmware that may be accessed and executed by processors to, in part or in whole, perform the acts of the methods described herein (e.g., so that the processor 116 is configured to communicate with provide the user interfaces of FIGS. 4, 7 and 8 discussed herein). Further, the architecture of the systems for both the ultrasound machine and multi-purpose electronic device are further described in FIG. 11.

Figure 9:
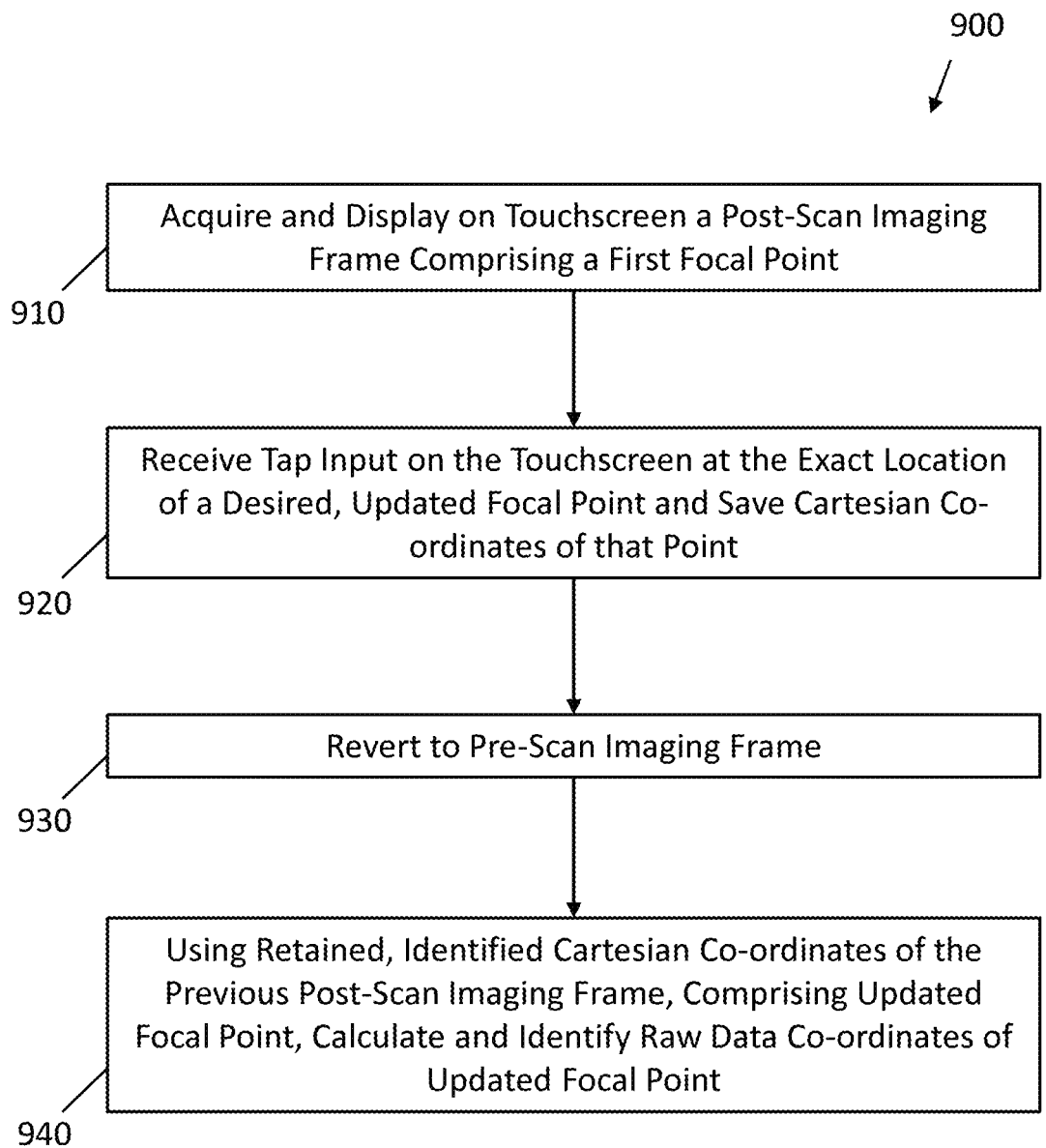
FIG. 9 is a flowchart diagram for steps of a method for adjusting/setting a focus and in accordance with at least one embodiment of the present invention.
Figure 10:
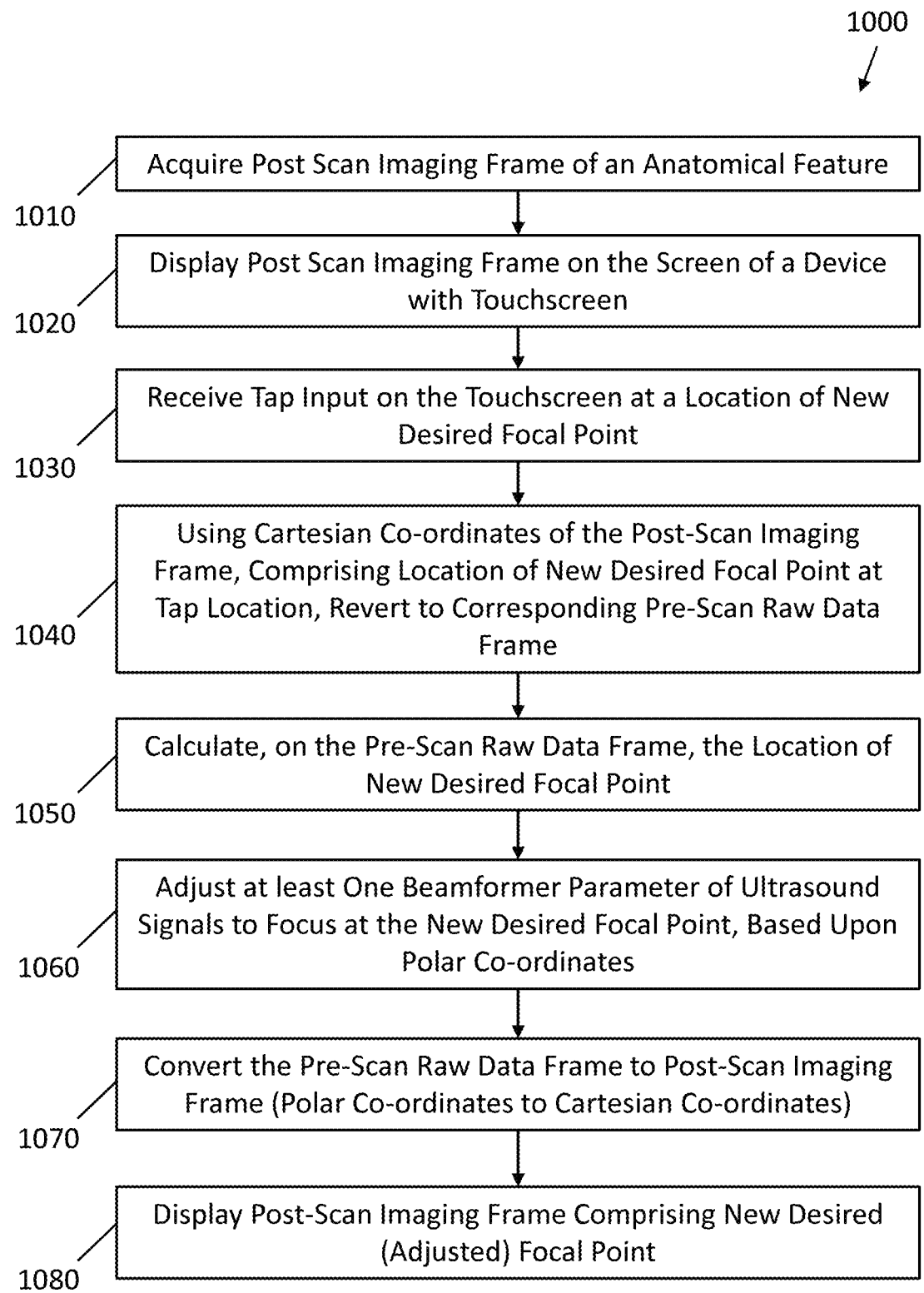
FIG. 10 is an additional flowchart diagram for steps of a method for adjusting/setting a focus and in accordance with at least one embodiment of the present invention.
Figure 11:
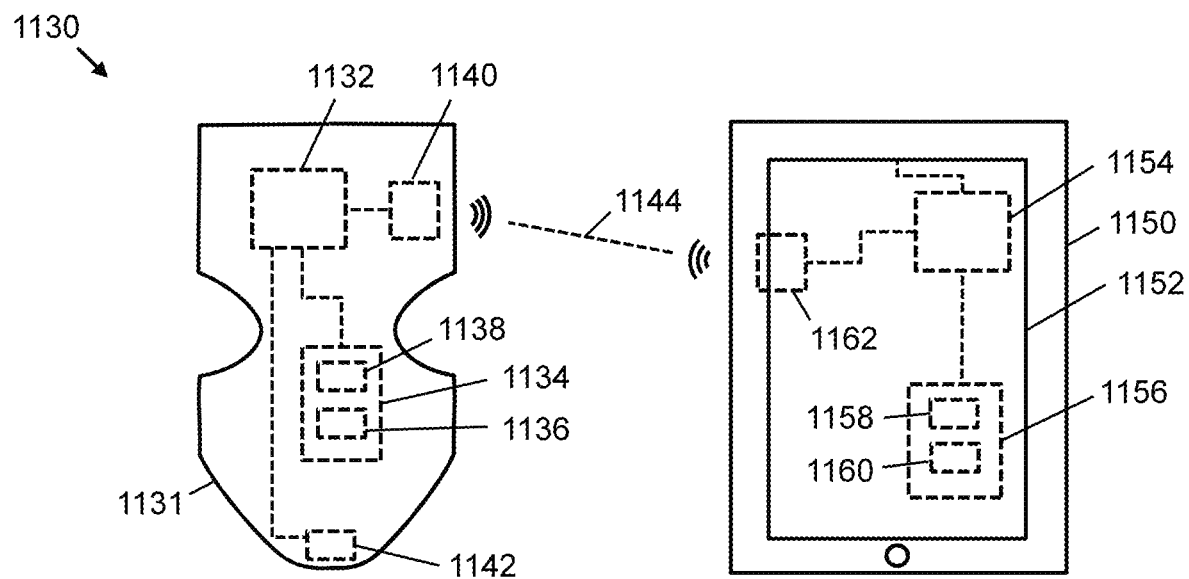
FIG. 11 is a schematic diagram of an ultrasound imaging system, according to an embodiment of the present invention.

As noted, the ultrasound imaging system 100 of FIGS. 1 and 1130 of FIG. 11 may be configured to perform the method of FIGS. 9 and 10, so as to receive a tap gesture input at a location directly on the ultrasound image feed on the touchscreen display, such location indicating on the post scan converted ultrasound image frame a desired focal adjustment point. The discussions below will be made with simultaneous reference to FIGS. 1 and 11, to illustrate how such components may be involved in performing various acts of the method of FIGS. 9 and 10. Steps of method 900 (FIG. 9) and 1000 (FIG. 10) may be implemented as software or firmware contained in a program memory or storage devices accessible to a processor 1154 of the multipurpose electronic device/display device 1150 and/or a storage device accessible to processor 1132 (116 in FIG. 1) of ultrasound scanner 1131 (101 in FIG. 1).

Figure 2:
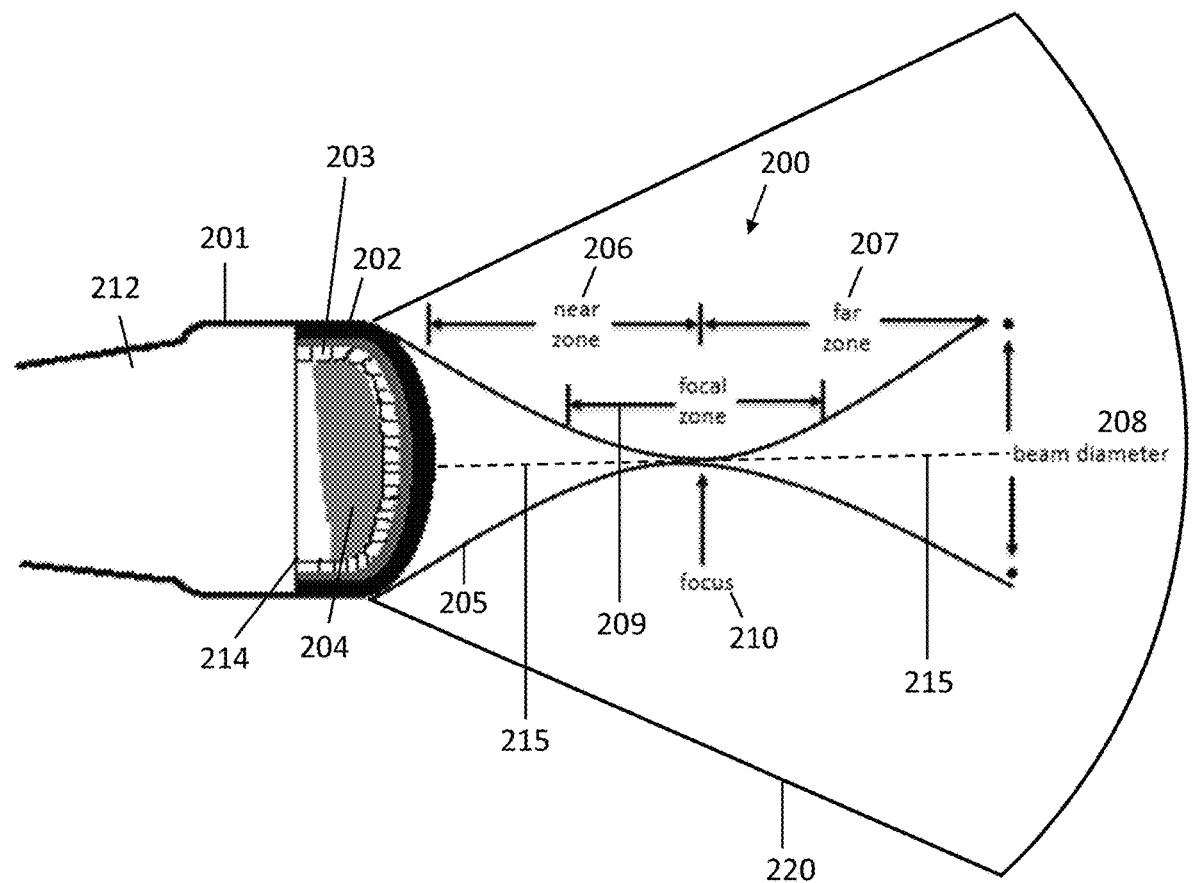
FIG. 2 shows an illustration including focal point and the boundaries of a focal zone created by a curvilinear ultrasound transducer.

Referring to FIG. 2, shown, generally as 200, an illustration of an ultrasound transducer 201 for use in accordance with the method and system of the invention (comprising body 212, thin acoustic insulator 214, a thin matching layer 202, piezoelectric elements 203) and the focal zones of ultrasound waves derived from the ultrasound transducer (having beam diameter 208). FIG. 2 shows the natural narrowing of the ultrasound beam 205 at a certain travel distance in the ultrasonic field, defining a transition level/focal zone 209 between near field/zone 206 (also called the Fresnel Zone) and far field/zone 207 (also called the Fraunhofer Zone) in relation to the ultrasound transducer 201. Within focal zone 209 is focus or focal point 210). The beam diameter at the transition level is equal to half the diameter of the transducer. At the distance of two times the near-field length, the beam width reaches the transducer diameter. The angle of the near field path to the far field path is called the divergence angle θ. As such axial resolution is best viewed in the near field and lateral resolution occurs best with narrow ultrasound beams. The maximal point of resolution is called the focal point, which represents the transition point between the near field and the far field. It is important to note that as a focal point size is decreased to improve the axial resolution, the divergence angle increases.

By way of this illustration of ultrasound transducer 201, which is a curvilinear probe, and the curvilinear image 220 it produces, it can be seen that the deeper an image is, the more likely that it is wider than the actual footprint of the probe. As such, the width of the image is equal to the ultrasound probe footprint size only at the uppermost part of the image, and any depth marks (which would be represented on the on the side of a user interface screen as shown for example in FIGS. 4-8, are pertinent only for measurement of the depth on the line drawn through the middle of the probe, shown in a hatched line as centre line 215. This inaccuracy or incongruence of the actual depth of an anatomical feature as it is displaced right or left of centre line 215, for the purpose of easily adjusting a focal point (210), is core aspect of the method and system of the invention.

Figure 3:
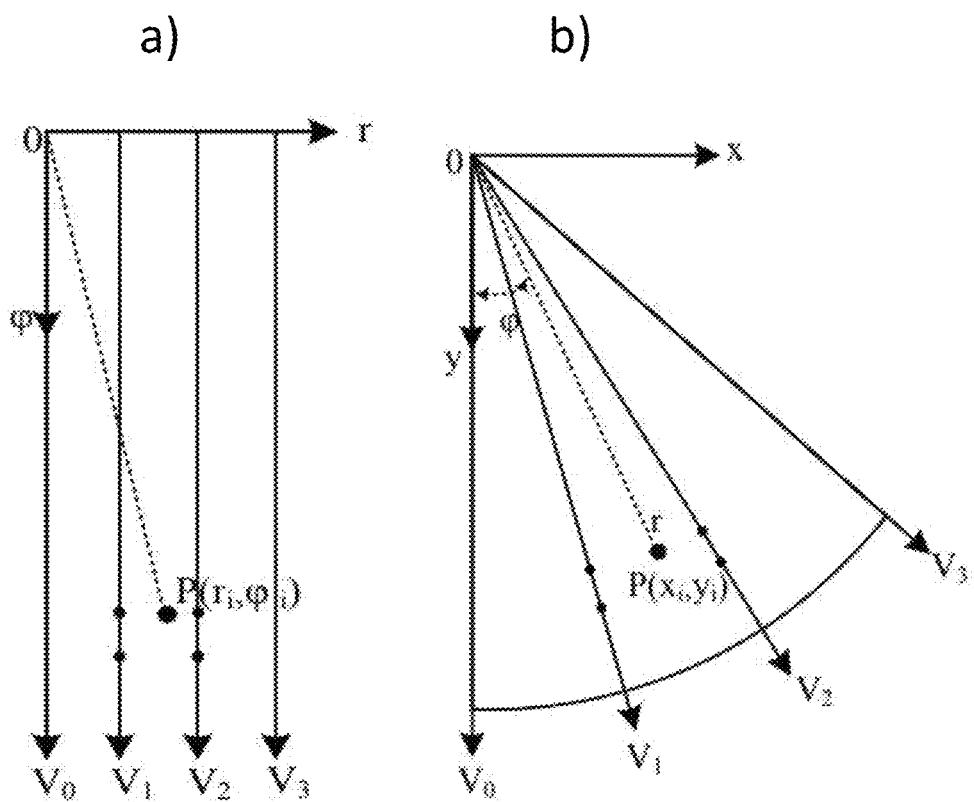
FIG. 3 is a representation of a polar coordinate system (a) on the left and a cartesian coordinate system (b) on the right.

Further to understanding the advantage of the focal point adjustment method of the present invention is FIG. 3, a model graph of Cartesian coordinates and polar coordinates. A sample point of Cartesian coordinates is shown as P ($x_i$, $y_i$) in FIG. 3b), which $x_i$ and $y_i$ are expressed as horizontal coordinates and vertical coordinates of Cartesian coordinate system. A sample point of polar coordinates as P($r_i$, $\varphi_i$) is shown in FIG. 3a), which $r_i$ and $\varphi_i$ are expressed as the polar radius and polar angle. The mathematical expression of polar coordinate to Cartesian coordinate system can be expressed as:

$$\begin{cases} x_i = r_i \cos\varphi_i \\ y_i = r_i \sin\varphi_i \end{cases}$$

As noted above, since the complex signal appearing in polar coordinates, from a raw ultrasound data image feed is in a format that cannot be output on a user display screen, it is vector-interpolated to a signal in cartesian coordinates (i.e., rasterization of vector data), which is a format which can be output by a scan conversion and shown on a screen grid. The scan conversion processor (for example 116 in FIG. 1) is any now known or later developed processor, such as a general processor, application specific integrated circuit, digital signal processor, digital circuit, analog circuit or combinations thereof. In some embodiments, the scan conversion processor is a graphics processing unit which may include a vertex processor, an interpolator, a fragment processor and a display buffer. The scan conversion processor is operable to identify acquired ultrasound data as a function of acquisition format values and operable to interpolate display values from the identified acquired ultrasound data. For example, the scan conversion processor is operable to determine display coordinates of interest for a plane in a volume or for a plurality of rays through the volume. The acquired ultrasound data is identified by inputting the display coordinates of interest into a look-up table. According to preferred embodiments, a look-up table-based method is used for real-time scan conversion ultrasound input data from polar coordinates to cartesian coordinates, to generate raster data and render such data as 2D images, 3D volumes, etc. . . . onto a user interface display. The look-up table is a memory or buffer and has values corresponding to a spatial conversion from the display format (cartesian) to the acquisition format (polar), such as, for example, storing the polar coordinates indexed by the cartesian coordinates. The cartesian coordinates may also index other values in addition to fixed point coordinates (e.g., R and Theta values of the polar coordinates format), such as a Boolean Flag indicating whether the dataset corresponds to a location outside a particular scanned region and/or an integer sum for other processing.

Turning back to FIG. 3, an image comprising a polar coordinate P(ri, φi) which is not suitable for grid display as a resultant image would be distorted (collapsed and having parallel scan lines, i.e. no widening with depth) compared to the expected wide and full spectrum viewing of such an image on an interface as acquired by a curvilinear scanner (widening with depth). The result of such scan conversion (in FIG. 3b) is an image instead comprising the shown cartesian coordinate P (xi, yi).

The method and system of the present invention, enables a simple tap gesture directly at a selected location on a post-scan converted ultrasound image frame of an anatomical feature/structure scanned using a curvilinear probe, to accurately and easily adjust one or more focal points. The method and system of the present invention address the aforementioned problems of accurate adjustment of focal point on a curvilinear image, particularly away from a centre line, due to widening of the displayed image at depth and line/data point distortion due to this arc. This is achieved, in part, by reverting the post scan converted ultrasound image frame comprising the location of the desired focal adjustment point, by way of the cartesian co-ordinates, to its corresponding pre-scan raw ultrasound data frame, and then calculating on the pre-scan raw ultrasound data frame, the location of the desired focal adjustment point, by way of polar co-ordinates of the desired focal adjustment point. Thereafter, at least one beamformer parameter of ultrasound signals being used to transmit and receive the ultrasound image may be appropriately adjusted to focus on the desired focal adjustment point, based upon the polar coordinates. These steps of reverting to raw data format and using polar coordinates to adjust the beamformer parameters obviates any issues with the location of the tap gesture or touch point, meaning that any point on the entire curvilinear image may be tapped and an accurate refocusing on that desired anatomical feature is attained. From a user perspective, this intuitively provides accurate focal point adjustments, without necessitating the use of a sliding scale or other depth-related and possibly inaccurate interface inputs.

Figure 4:
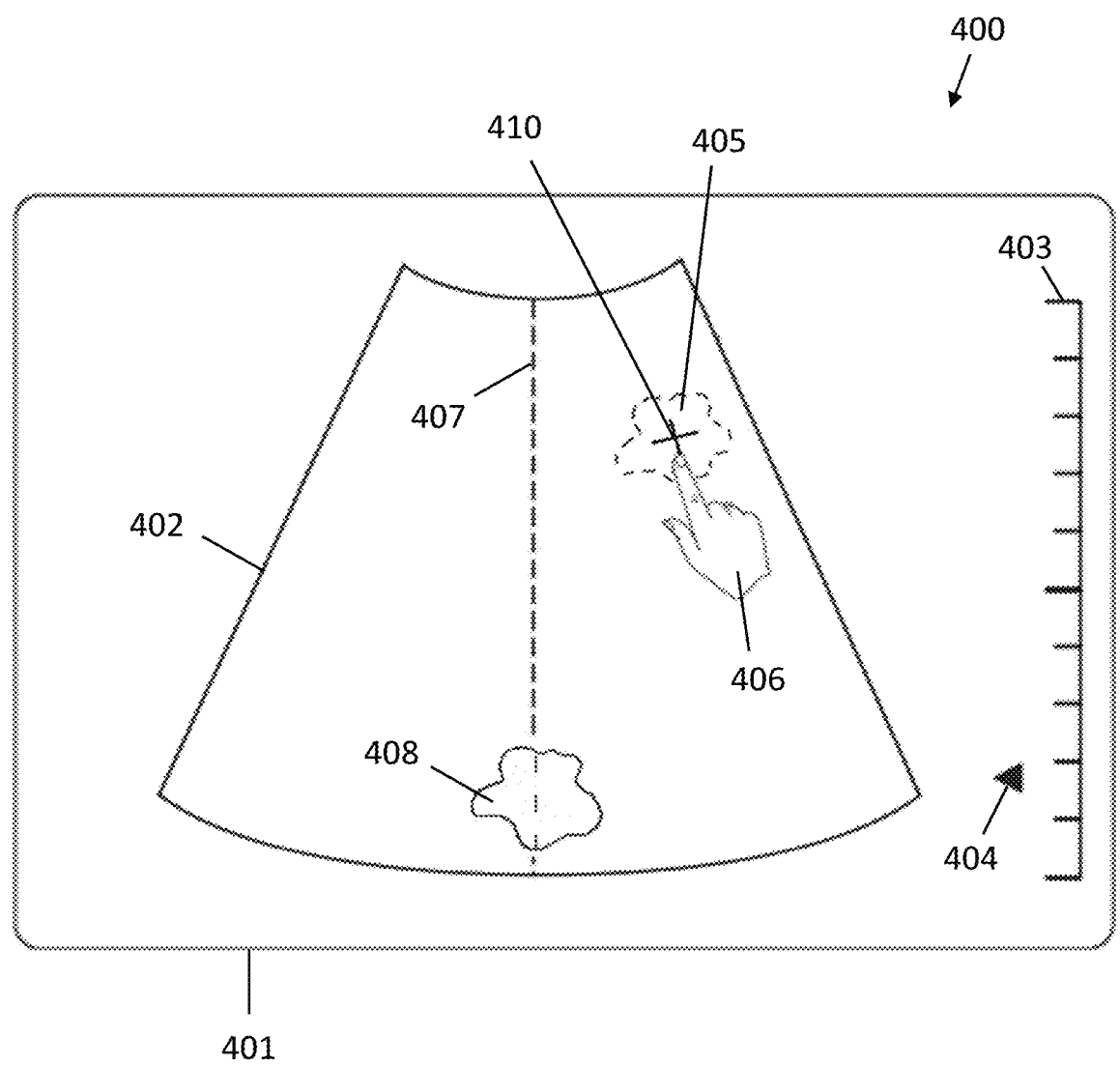
FIG. 4 is an example of a user interface of an ultrasound system that receives input via a tap gesture on the ultrasound image, in accordance with at least one embodiment of the present invention, showing a user hand tapping a selected point on the ultrasound image.

FIG. 4 is an example user interface 401 of an ultrasound system (generally indicated at 400) that receives input via a single tap gesture, in accordance with at least one embodiment of the present invention, in order to activate an automatic focal point adjustment. Whereas traditional ultrasound systems require users to adjust focus and depth using 'up' and 'down' buttons or a sliding scale activated by various drag motions (all such options located on an interface screen to the side of the displayed ultrasound image frame), the use of a single tap gesture directly on the ultrasound image using the method and system of the present embodiments greatly enhances accuracy, user efficiency and ease-of-use. At mark 410 there is shown a user directed tap gesture on the curvilinear ultrasound image feed 402, on interface 401, having depth scale 403 and (for visual reference only) hatched line 407 representing the centre of curvilinear ultrasound image feed 402. The curvilinear ultrasound image feed 402 shows an anatomical feature 408 already in clear focus, in solid non-fuzzy lines and indicator arrow 404 illustrating focal depth of this anatomical feature. In respect to anatomical feature 408, focal depth shown by indicator arrow 404 is visually aligned with actual depth, due to the proximity to the centre line of anatomical feature 408 (such depths being true to image, for reasons described above in FIG. 2 and FIG. 3). In accordance with the method of the invention, an extended finger of a user hand 406 taps directly on the curvilinear ultrasound image feed 402, at region/anatomical feature 405 (generally comprising mark 410, a new desired focal point on an anatomical feature), such region shown in fuzzy, as yet unfocussed lines, prior to applying the further focal point adjustment steps of the invention, as set out in both FIGS. 7 and 8 (via schematics of the interface) and FIGS. 9 and 10 (via method acts/flow charts).

Figure 5:
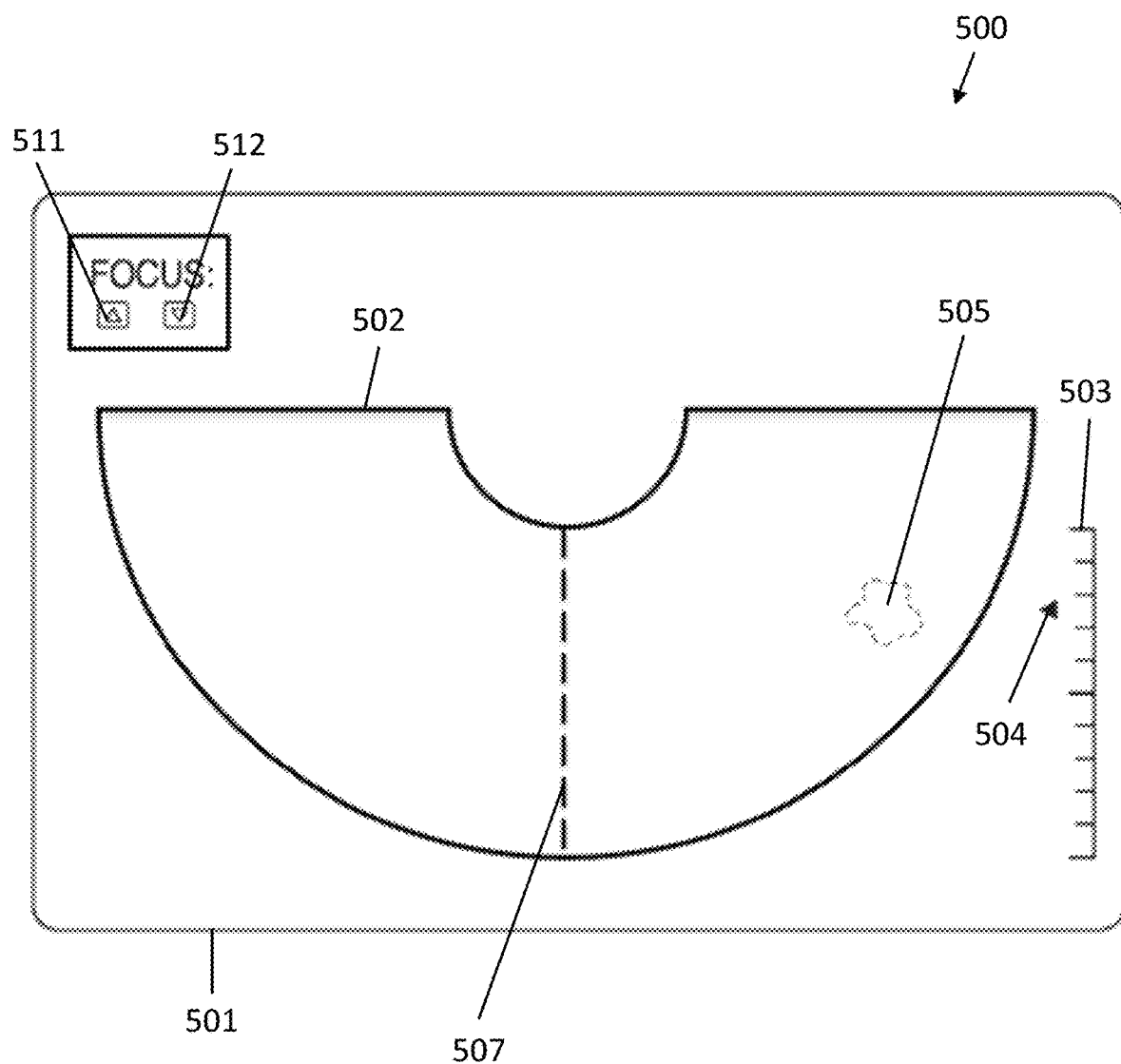
FIG. 5 is an example of a prior art user interface of an ultrasound system that receives input as to focal point adjustment by way of up/down arrow buttons.
Figure 6:
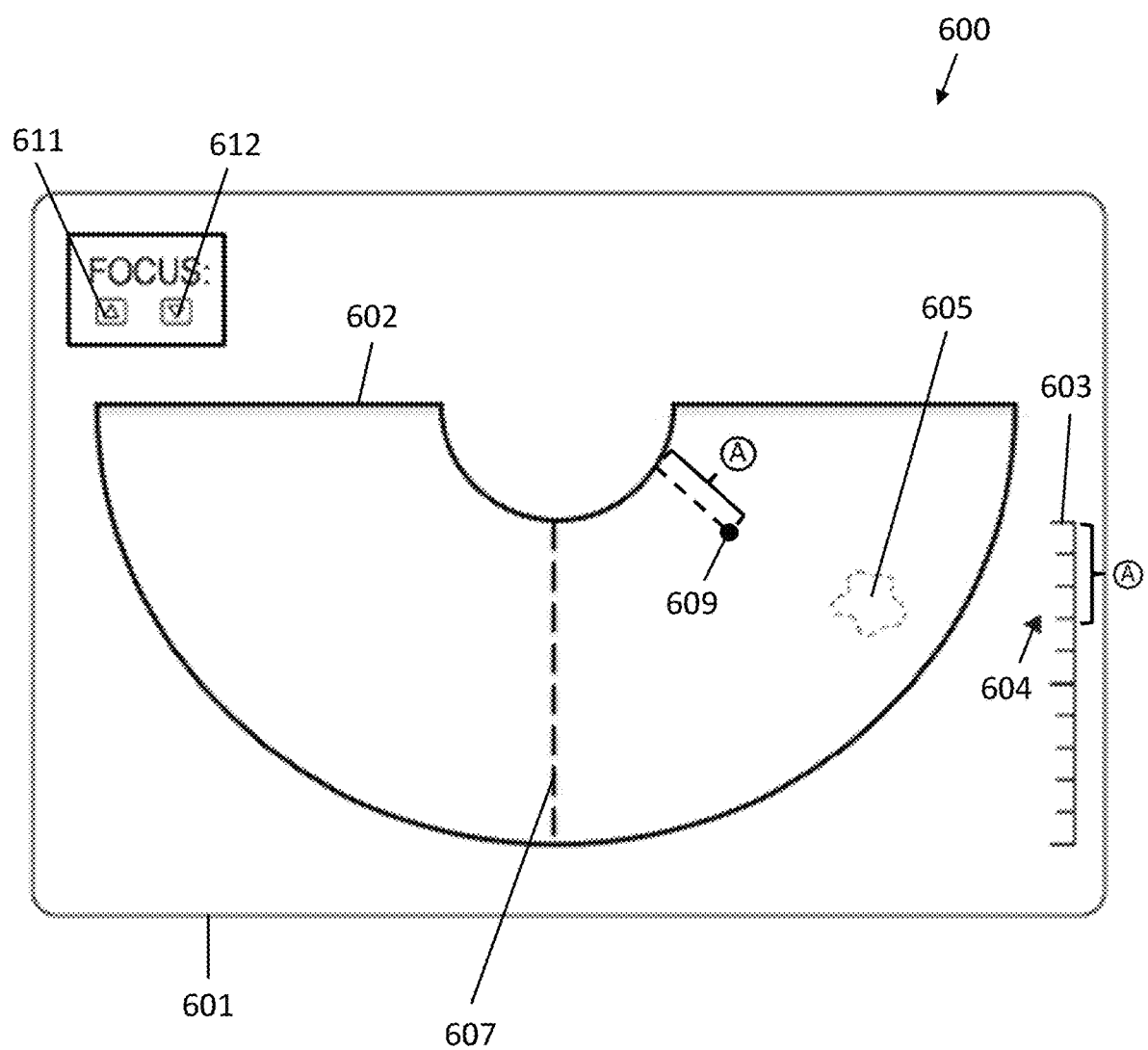
FIG. 6 is an example of a prior art user interface of an ultrasound system that receives input via as to focal point adjustment by way of up/down arrow buttons, showing incorrect placement of adjusted focal point.
Figure 7:
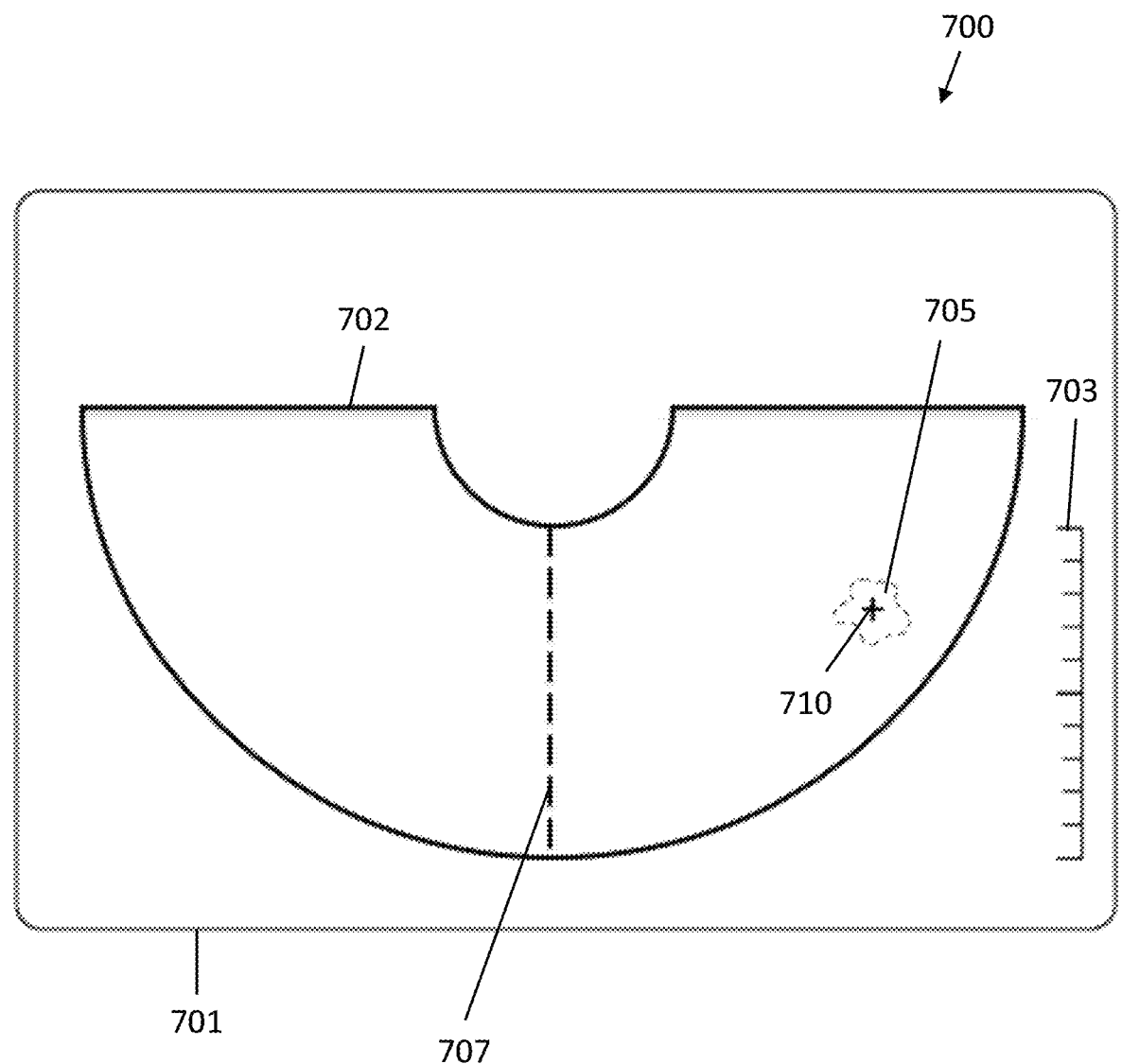
FIG. 7 is an example of a user interface of an ultrasound system that receives input via a tap gesture directly on the ultrasound image, in accordance with at least one embodiment of the present invention.
Figure 8:
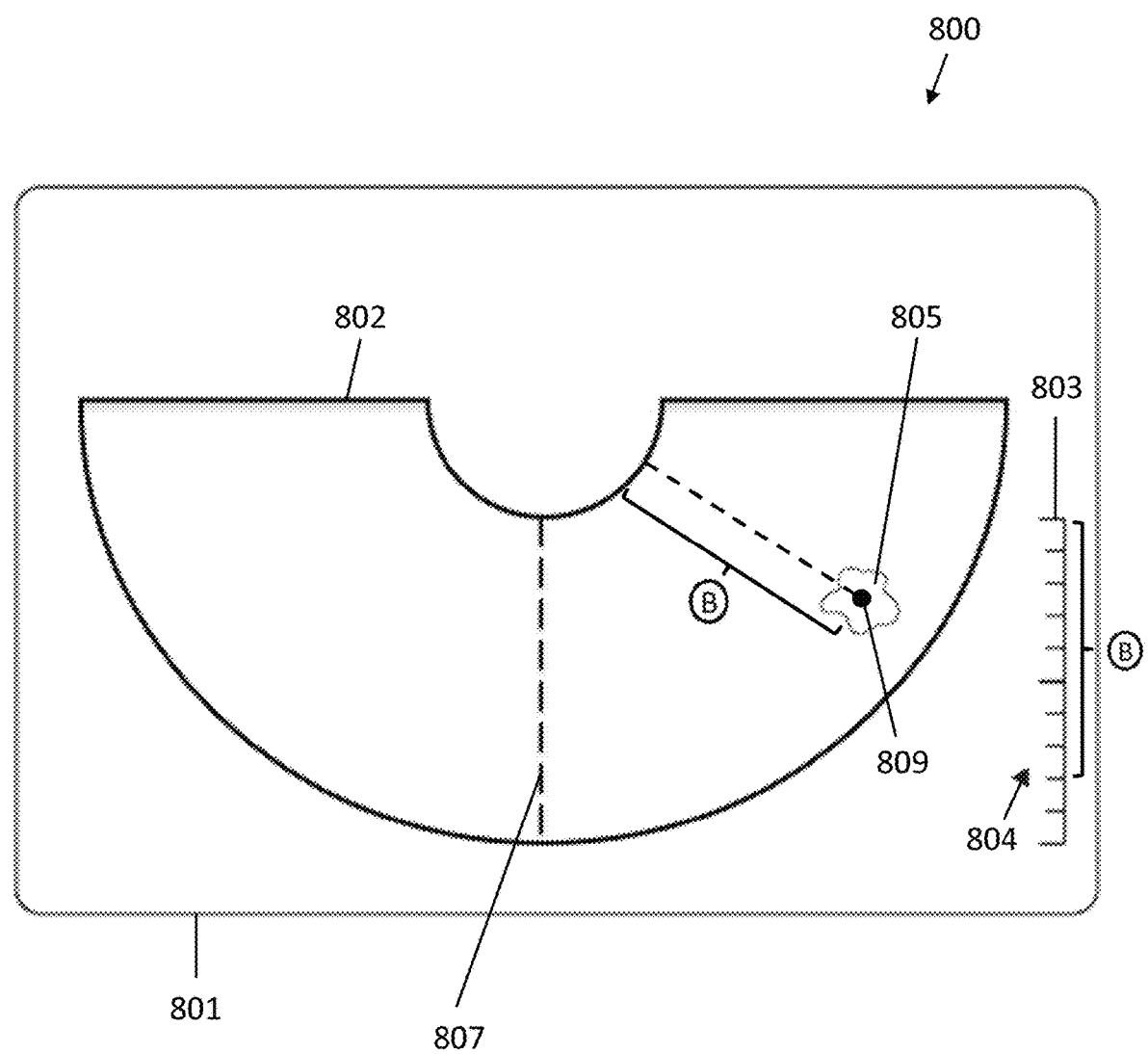
FIG. 8 is an example of a user interface of an ultrasound system that receives input via a tap gesture directly on the ultrasound image, in accordance with at least one embodiment of the present invention showing correct placement of adjusted focal point and depth representation.

Referring to FIGS. 5-8, shown there generally as 500, 500, 700 and 800 a series of user interface interactions for receiving input to adjust a focal point on a user interface (501, 601, 701 and 801). Each ultrasound image feed on the user interface is non-linear, acquired by way of example using an endoscopic ultrasound transducer, (502, 602, 702 and 802) and a depth indicator (503, 603, 703 and 803) is shown on a side of each image feed. Focus position is illustrated in FIGS. 5, 6 and 8 by a triangle marker (504, 604 and 804). An ultrasound image feed acquired using an endoscopic ultrasound best illustrates the method of the invention, due to the wide shape of the feed, however it is to be understood that any type of ultrasound image feed benefits from the present invention.

FIGS. 5 and 6 exemplify one of the key problems in the art, wherein a user of an ultrasound scanner adjusts a focal point using traditional slider on the depth control scale (shown as 503) for example by using triangle marker 504 as a touch point on the user interface for sliding changes to a focal point. Alternatively, in some prior art systems and as also shown herein for illustration, there are separate up and down buttons (511 and 512) to toggle and adjust the position of triangle marker 504 relative to depth indicator 503. To change the focal point manually, a user would conventionally expect to use these on-screen controls 511 and 512 in a manner shown in FIGS. 5 and 6 to move triangle marker 504 up and down the depth control scale. Shown in FIG. 5 is anatomical feature 505 on ultrasound image feed 502 which user is desirous to be in focus (hence shown as out of focus with fuzzy/blurred lines) and such user would employ buttons 511 and/or 512 to move triangle marker 504 thereby to select a location for the desired focal point adjustment, at 505, such adjustment being an attempt to get anatomical feature 505 in focus.

FIG. 6 illustrates the result of the attempted focal point manual adjustment from FIG. 5 using up/down buttons 511 and/or 512 (shown as and equivalent to buttons 611 and 612) to move triangle marker 504/604. The desired anatomical feature is shown as 605 (analogous to 505 in FIG. 5) and remains out of focus with fuzzy/blurred lines despite attempted focal point adjustment using buttons 511/611 and/or 512/612. While a user made a desired focal point adjustment, lining up triangle marker 604 using up/down buttons 511/611 and/or 512/612 at what visually appears to be the correct location for focusing desired anatomical feature 605 (analogous to 505 in FIG. 5), the actual distance (shown with length A) for focal point adjustment is incorrect and the adjusted focal point ends up as point 609 ("actual focal point"), a distance away from the desired anatomical feature 605. Length A is shown along the depth indicator 603 (as adjusted by the user) and separately on the ultrasound image feed 602 itself (both being of the same length) arriving at point 609. The difference in the user selected focal point (at user directed placement of triangle marker 604) and actual focal point can be accounted for due to widening of the non-linear image (see also FIGS. 2 and 3) such that a selected focal point may be inaccurate and is most likely inaccurate the farther from the centre line 607 the desired focal point adjustment sought to be made is. In other words, within the prior art, a user manually adjusting a focal point by way of, for example, buttons 511/611 and/or 512/612, to align with desired anatomical feature 605 does not properly adjust focal point to that desired location but in fact a location point 609. Desired anatomical feature 605 thus remains blurred and unfocussed and an entirely undesired area at 610 is adjusted to be in focus based upon user inputs, as described above.

In contrast to the focal point misalignment described above, a benefit to the method of the invention is illustrated in the sequence shown in FIGS. 7 and 8. Shown generally as 700 in FIG. 7, within non-linear (endoscopic) ultrasound image feed 702, is anatomical feature 705 which a user is desirous to be in focus (hence out of focus with fuzzy/blurred lines) and which such user engages with a tap gesture at focal point 710 within anatomical feature 705. FIG. 8 illustrates the result and next steps of that focal point tap adjustment from FIG. 7. In FIG. 8, desired focal point 809 (analogous to 710) has thereby been adjusted in accordance with the method of the invention, so that anatomical feature 805 (analogous to 705), comprising focal point 809, is represented in solid (in focus) lines. Triangle marker 804 (focal indicator) represents the true depth of the desired focal point (not a user selected depth as shown in FIGS. 5 and 6) and it can be seen that this is at depth represented by length B. Length B is shown along the depth indicator 803 and separately on the actual ultrasound image feed 802 itself (both being of the same length) arriving at focal point 809. As such, FIGS. 5-8 illustrate the incongruence between user selected (incorrect) depth for a new focal point and a user simply tapping a point on an ultrasound image feed for an automatic and accurate focal point adjustment, wherein focal point coordinates are reverted prior to beamformer modifications, in accordance with the method and system of the invention.

Referring to FIGS. 9 and 10, shown generally as 900 and 100 are flowchart diagrams for parts of the acts of a method for adjusting a focal point on an an ultrasound image feed comprising a post scan converted ultrasound image frame, using a tap gesture directly on the on the ultrasound image feed on the touchscreen display, such location indicating on the post scan converted ultrasound image frame a desired focal adjustment point in accordance with at least one embodiment of the present invention. More specifically, the acts at 900 relate to receipt of a tap gesture input and coordinate conversion and the acts at 1000 additionally comprises steps of beamformer adjustment and display.

The method may be performed by a computing device (such as, for example, 1150 in FIG. 11) having a touchscreen display configured to communicate with an ultrasound transducer (such as, for example, 1131 in FIG. 11) and to display ultrasound images. In discussing the method of FIG. 9 and FIG. 10, reference will simultaneously be made to the example user interfaces shown in FIGS. 7 and 8.

At act 910, an ultrasound image is acquired and displayed on a touchscreen, such as on display/interface screen 126 (FIG. 1), wherein such image is a post-scan ultrasound imaging frame comprising a first focal point, generally having been prior selected to view a particular anatomical feature.

This ultrasound image data post-scan ultrasound imaging frame may be obtained, for example, by ultrasound machine 101 employing a high frequency, high voltage pulse to excite transducer 102 to emit ultrasound waves and receiving the reflected ultrasound waves. In particular embodiments, the ultrasound machine 101 may be a probe which acquires ultrasound image data by generating pulses of a specified amplitude in accordance with an ultrasound sequence specified in a sequence table. The probe may perform ultrasound beam generation using transmit beamforming, detects and receives the ultrasound echo and performs receive beamforming, and processes the data based on the sequence specified in the sequence table. The probe may transmit the processed ultrasound image data to a multipurpose electronic device 120 with display 126 (FIG. 1) which has a processor 1154 (FIG. 11) that further processes the data for display (e.g. scan conversion) and then displays the ultrasound image on the output component (e.g., screen) 126.

Similarly, at act 1010, a post-scan imaging frame of an anatomical feature is acquired and at 1020 such post-scan imaging frame is displayed on a screen of a device with a touchscreen, such as display/interface screen 126 (FIG. 1) and/or screen of display device 1150 (FIG. 11).

At act 920 and 1030, desirous of acquiring a new, updated focal point, a tap gesture input is received on the touchscreen, on the ultrasound image at the exact location of the desired, updated focal point. FIG. 4 provides an illustration of such a tap gesture (on mark 410) by hand 406, although it is to be understood that tap gesture indicating mark 410 can be made and act 920 and act 1030 implemented with a stylus or other user interface touch device/tool, as well as a user hand/finger. The touchscreen interface may receive this input and provide it to processor 1154 (FIG. 11) which executes software instructions to analyse the input and determine the command associated with the input. Further, receipt of this tap gesture input triggers an act of saving the cartesian co-ordinates of the desired, updated focal point. It can also be seen that the anatomical feature 404 surrounding mark 410 is in blurred/fuzzy outline, indicating non-focusing of that area. Similarly, anatomical feature 705 surrounding mark 710 is in blurred/fuzzy outline, indicating non-focusing of that area. Each mark 410 and 710 on FIGS. 4 and 7 respectively, representing the on-screen tap gesture, serves to trigger the next sequential steps in focal point adjustment.

These next sequential steps may include process 1154 in the multipurpose electronic device, comprising the display (touchscreen display) 126 to may transmit the command to save the cartesian coordinates of the tapped focal point, revert the post-scan imaging frame to a pre-scan raw data frame and to calculate, one the pre-scan raw data frame the location of the new desired focal point, using its polar coordinates. All this may be achieved via one or more communication interfaces between the ultrasound traducer and the multipurpose electronic device (such as, for example, via data link 118).

Act 930 in FIG. 9 and act 1040 in FIG. 10 involve reverting the post scan converted ultrasound image frame comprising the location of the desired focal adjustment point, by way of the saved cartesian co-ordinates, to its corresponding pre-scan raw ultrasound data frame. Back converting alters the post-scan converted ultrasound image, as represented in x-y coordinates suitable for human viewing on an interface, to the polar coordinate system of the raw ultrasound data frame from which the post-scan converted ultrasound image was originally scan converted. The back conversion includes, for example, transforming the coordinates of the tap gesture marking to the coordinate system of the raw ultrasound data frame and associating them with the raw ultrasound data frame that was scan converted to result in the scan converted ultrasound data frame.

In FIG. 9, at act 940 and in FIG. 10 at act 1050, the location of the desired focal adjustment point is calculated, by way of polar co-ordinates of the desired focal adjustment point, on the pre-scan raw ultrasound data frame. Generally, although not exclusively this calculation, and others related to each of these acts described in FIGS. 9 and 10 may be achieved by processor 1154 (including through the operation of a cloud-based application in communication with or functionally uploaded onto the multipurpose electronic device).

FIG. 10, act 1060 provides for the subsequent adjustment of at least one beamformer parameter of ultrasound signals to focus the new desired focal point, based upon the polar coordinates. More specifically, the at least one beamformer parameter relates to transmit beamforming. Transmit beamforming, at a selectable focal distance is achieved by specific timing delays among the active transducer elements, each with a known concave excitation profile. A focal zone close to the transducer surface is produced by initially firing the outer transducer elements in the active array and incrementally firing the inner elements to the center element with slightly longer delays using a concave excitation pattern. A more distant focal zone is achieved by reducing the delay time differences among the transducer elements with a shallow concave excitation pattern, resulting in beam convergence at a greater depth. The beamformer in the ultrasound transducer controls the excitation patterns, with the focal zone depth being selectable or calculated automatically, in accordance with the focal point adjustment method of the invention. The beamformer controller begins with the first scan line and excites an array of piezo-electric transducers with a sequence of high voltage pulses via transmit amplifiers. Typical performance numbers for the amplifiers is ±100 V and ±2 Amps for each piezo-electric element (203 in FIG. 2). The pulses go through a transmit/receive (Tx/Rx) switch (106 in FIG. 1), which prevents the high voltage pulses from damaging the receive electronics. Note that these high voltage pulses have been properly time delayed so that the resulting sound waves can be focused along the desired scan line to produce a narrowly focused beam at the desired focal point. The transmit beamformer controller (122 in FIG. 1) determines which transducer elements to energize at a given time and the proper time delay value for each element to properly steer the sound waves towards the desired focal point. As the sound waves propagate toward the desired focal point, they migrate through body materials with different densities. With each change in density, the sound wave has a slight change in direction and produces a reflected sound wave. Some of the reflected sound waves propagate back to the transducer and form the input to the piezo-electric elements in the transducer. The resulting low voltage signals are scaled using a variable controlled amplifier (VCA) before being sampled by analog-to-digital converters (ADC, 110 in FIG. 1)). The VCA is configured so that the gain profile being applied to the received signal is a function of the sample time since the signal strength decreases with time (e.g., it has traveled through more tissue). The number of VCA and ADC combinations determines the number of active channels used for beamforming.

As described above, ultrasound beams leave the transducer at the same width as the face. They travel through the near zone before narrowing at a focal zone and widening in the far zone. The resolution, or the ability to discern two closely situated objects, and lateral resolution is best in the focal zone. Spatial resolution can also be improved with higher frequencies, smaller pulse repetition frequencies, and short pulse duration. The axial resolution, or the ability to discern two structures in the path of the beam, is generally better than lateral resolution, or the ability to distinguish two side-by-side structures due to ultrasound beams being shorter than they are wide. Lateral resolution is greatest at the focal point where the beam width is most narrow. Temporal resolution, or the time the machine takes to create an image, is inversely related to the frame rate. Higher frame rates produce lower resolution images, and lower frame rates have higher resolution images. Frame rates of at least 15 frames per second produce real-time images wherein temporal resolution is most important with moving objects.

Act 1060 involves adjusting at least one transmit beamformer parameter of the ultrasound signals which may affect the timing and sequence (sum and delay) in which the piezoelectric elements are selected to be pulsed to allow a beam to be formed during a transmit beamforming function. Corresponding sum and delay operations can then be considered during reception to form one or more lines in a generated ultrasound image.

Examples of transmit beamformer parameters that can be adjusted and manipulated at act 1060 include but are not limited to: i) Spatial resolution: the smallest spatial distance for which two scatterers can be distinguished in the final image. Spatial resolution can be either axial (along the direction of propagation of the ultrasound wave), lateral, or elevation resolution (along the plane to which the direction of propagation is perpendicular). This feature is normally expressed in mm. ii) Temporal resolution: the time interval between two consecutive images. This feature is normally expressed in Hz. iii) Contrast: the capability to visually delineate different objects, e.g., different tissue types, in the generated images. This feature is generally expressed in dB, and it is a relative measure between image intensities. iv) Penetration depth: the larger depths for which a sufficiently high signal-to-noise ratio (SNR) level can be maintained. This feature is normally expressed in cm. v) Array aperture: the physical sizes of the surface representing the combined distribution of active and passive ultrasound sensors: in other words, the array footprint. The array aperture is defined by the number of ultrasound sensors (elements), their sizes, and their distribution. This feature is generally expressed in $cm^2$. vi) Field of view (FOV): the sizes of the area represented by the obtained images. This feature is generally expressed in $cm^2$ or $cm^3$. vii) Frame rate (FR): the frame rate of an imaging system determines how well it can capture rapid object motion. Ultrasound images require pulsed transmissions in several scan line directions and each scan line requires waiting for echoes as the sound propagates through the body, which means that the sound limits how rapidly ultrasound images can be acquired. For example, for an imaging depth of 15 cm, each transmitted pulse has to travel 30 cm at 1540 m/s. Hence each ultrasound scan line requires 0.19 ms of acquisition time. A typical 2D ultrasound image is constructed from approximately 100-200 scan lines across an imaging sector and each ultrasound frame is then recorded in 0.02-0.04 seconds, which corresponds to 25-50 frames per second.

Beamformer parameters that may additionally or alternatively be modified at act 1060 include filter frequency and/or sampling frequency. The frequency of ultrasound signals used to acquire ultrasound images may be adjusted depending on the inputted imaging depth. In various embodiments, as the transmission frequency is being adjusted based on the imaging depth change, the receive frequency may also be adjusted to match the transmission frequency. Additionally, or alternatively, the receive sampling frequency can be optimized to match the number of ultrasound samples taken to the vertical pixels in the display area. For example, this may remove potential aliasing and/or enhance optimization of image processing algorithms post beamforming.

Referring back to FIG. 10, at act 1070, in order for the new desired focal point to be displayed on an interface screen, the pre-scan raw data frame is converted to a post-scan imaging frame (i.e., from polar coordinates back to grid-friendly cartesian coordinates and at act 1080 such post scan converted image frame is displayed on the screen. This scan conversion may then be performed on the data to transform the image data in a manner that allows it to be displayed in a form that is more suitable for human visual consumption. For example, this may involve converting the image data from the data space (e.g. polar coordinate form) to the display space (e.g. Cartesian coordinate form). The acquired ultrasound images may be displayed on the display 126 of multipurpose electronic device 120 (act 10804 of FIG. 10). Scan conversion is one of the actions that renders the image data suitable for display. However, as will be apparent to those of skill in the art, other technological steps may also need to be performed, such as, for example, amplification and/or digitization of the data. After the scan conversion, an ultrasound image may be displayed by the electronic display unit 802.

In a further embodiment of the method of the invention, the tap gesture (shown as markers 410 and 710) on the post scan converted ultrasound image frame, representing the desired focal adjustment point, is defined by pixels comprising a set of x, y coordinates on a cartesian space and the corresponding pre-scan raw ultrasound data frame is defined by a radial line and angle in a polar space ("polar coordinate"), and wherein the method comprises: verifying bounds of the polar coordinate ("verified bounds"); calculating depth based on sample inputs (wherein sample inputs=sampling rate+speed of sound) of the verified bounds; –calculating, using the depth, a new transmit focal point/aperture ("transmit beamformer"); acquiring new pre-scan raw ultrasound data frames based on the new transmit focal point/aperture; scan converting the new pre-scan ultrasound data frames comprising the new transmit focal point/ aperture to a new post scan converted ultrasound image frame; and finally displaying the new post scan converted ultrasound image frame with the new transmit focal point/aperture on the touchscreen display (126, for example).

Referring to FIG. 11, an exemplary system 1130 is shown for adjusting a focal point by tap gesture, in accordance with the present invention. The system 1130 includes an ultrasound scanner 1131 with a processor 1132, which is connected to a non-transitory computer readable memory 1134 storing computer readable instructions 1136, which, when executed by the processor 1132, may cause the scanner 1131 to provide one or more of the functions of the system 1130. Such functions may be, for example, the acquisition of ultrasound data, the processing of ultrasound data, the scan conversion of ultrasound data, the transmission of ultrasound data or ultrasound frames to a display device 1150, the detection of operator inputs to the ultrasound scanner 1131, and/or the switching of the settings of the ultrasound scanner 1131.

Also stored in the computer readable memory 1134 may be computer readable data 1138, which may be used by the processor 1132 in conjunction with the computer readable instructions 1136 to provide the functions of the system 1130. Computer readable data 1138 may include, for example, configuration settings for the scanner 1131, such as presets that instruct the processor 1132 how to acquire data and to collect and process the ultrasound data.

The scanner 1131 may include an ultrasonic transducer 1142 that transmits and receives ultrasound energy in order to acquire ultrasound frames. The scanner 1131 may include a communications module 1140 connected to the processor 1132. In the illustrated example, the communications module 1140 may wirelessly transmit signals to and receive signals from the display device 1150 along wireless communication link 1144. The protocol used for communications between the scanner 1131 and the display device 1150 may be WiFi™ or Bluetooth™, for example, or any other suitable two-way radio communications protocol. In some embodiments, the scanner 1131 may operate as a WiFi™ hotspot, for example. Communication link 1144 may use any suitable wireless communications network connection. In some embodiments, the communication link between the scanner 1131 and the display device 1150 may be wired. For example, the scanner 1131 may be attached to a cord that may be pluggable into a physical port of the display device 1150.

In various embodiments, the display device 1150 may be, for example, a laptop computer, a tablet computer, a desktop computer, a smart phone, a smart watch, spectacles with a built-in display, a television, a bespoke display or any other display device that is capable of being communicably connected to the scanner 1131. The display device 1150 may host a screen 1152 and may include a processor 1154, which may be connected to a non-transitory computer readable memory 1156 storing computer readable instructions 1158, which, when executed by the processor 1154, cause the display device 1150 to provide one or more of the functions of the system 1130. Such functions may be, for example, the receiving of ultrasound data that may or may not be pre-processed; scan conversion of received ultrasound data into an ultrasound image; processing of ultrasound data in image data frames; the display of a user interface; the control of the scanner 1131; the display of an ultrasound image on the screen 1152; the processing of a tap gesture input to the screen, the processing to revert the cartesian coordinates to polar coordinates, the processing to verifying bounds of the polar coordinate; the calculation of depth based on sample inputs (wherein sample inputs=sampling rate+speed of sound) of the verified bounds; and the calculation, using the depth, a new transmit focal point/aperture.

The screen 1152 comprises a touch-sensitive display (e.g., touchscreen) that can detect a presence of a touch from the operator on screen 1152 and can also identify a location of the touch in screen 1152. The touch may be applied by, for example, at least one of an individual's hand, glove, stylus, or the like. As such, the touch-sensitive display may be used to receive the tap gesture indicating at least one focal point adjustment. The screen 1152 and/or any other user interface may also communicate audibly. The display device 1150 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory 1156 may be computer readable data 1160, which may be used by the processor 1154 in conjunction with the computer readable instructions 1158 to provide the functions of the system 1130. Computer readable data 1160 may include, for example, settings for the scanner 1131, such as presets for acquiring ultrasound data and settings for a user interface displayed on the screen 1152. Settings may also include any other data that is specific to the way that the scanner 1131 operates or that the display device 1150 operates.

It can therefore be understood that the computer readable instructions and data used for controlling the system 1130 may be located either in the computer readable memory 1134 of the scanner 1131, the computer readable memory 1156 of the display device 1150, and/or both the computer readable memories 1134, 1156.

The display device 1150 may also include a communications module 1162 connected to the processor 1154 for facilitating communication with the scanner 1131. In the illustrated example, the communications module 1162 wirelessly transmits signals to and receives signals from the scanner 1131 on wireless communication link 1144. However, as noted, in some embodiments, the connection between scanner 1131 and display device 1150 may be wired.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

C. Claim Support

In a first broad aspect of the present disclosure, there is provided an ultrasound imaging system, comprising a touchscreen display; and a processor configured to execute instructions that cause the processor to provide a user interface on the touchscreen display, the user interface comprising an ultrasound image feed comprising a post scan converted ultrasound image frame; wherein upon receipt of input of a tap gesture at a location directly on the ultrasound image feed on the touchscreen display, such location indicating on the post scan converted ultrasound image frame a desired focal adjustment point, the processor causes the ultrasound imaging system to: revert the post scan converted ultrasound image frame comprising the location of the desired focal adjustment point, by way of the cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image to focus at the desired focal adjustment point, based upon the polar coordinates.

In some embodiments the at least one beamformer parameter is selected from the group consisting of focus position, number of focal zones, receive filter frequency, and receive sampling frequency.

In some embodiments relating to the system, the processor additionally causes the ultrasound system to: i) acquire pre-scan raw ultrasound data frames based on the at least one adjusted beamformer parameter; ii) scan convert the pre-scan ultrasound data frames comprising the desired focal adjustment point to a post scan converted ultrasound image frame; and iii) display the post scan converted ultrasound image frame with the desired focal adjustment point on the touchscreen display.

In some embodiments relating to the system the processor is communicatively coupled with a curvilinear ultrasound transducer.

In some embodiments relating to the system the touchscreen display shows a curvilinear ultrasound image feed, and a tap gesture on the touchscreen is at a location on or near an outer edge of the curvilinear ultrasound image feed.

In some embodiments relating to the system the beamformer is adjusted based upon a distance (radial coordinate) and an angle (angular coordinate) of the polar co-ordinates.

In some embodiments relating to the system the processor additionally causes the ultrasound system to respond to more than one tap gesture on locations directly on the ultrasound image feed on the touchscreen display, such locations indicating more than one, sequential desired focal adjustment point, each defined by differing axial depths.

In some embodiments relating to the system the entire ultrasound image feed on the touchscreen display is responsive to touch, to permit a user to input the tap gesture at any desired location for focal point adjustment.

In some embodiments relating to the system, the touchscreen display is part of a multi-purpose portable computing device.

In a second broad aspect of the present disclosure, there is provided a method for adjusting a focal point on an ultrasound image feed, acquired from an ultrasound transducer, the method comprising providing a touchscreen display on a multi-purpose electronic device, the touchscreen display showing the ultrasound image feed comprising a post scan converted ultrasound image frame; receiving a tap gesture at a location directly on the post scan converted ultrasound image frame on the touchscreen display, such location indicating a desired focal adjustment point, to modify the imaging depth of the ultrasound image feed; upon receipt of the tap gesture, revert the post scan converted ultrasound image frame comprising the location of the desired focal adjustment point, by way of cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image frame to focus at the desired focal adjustment point, based upon the polar coordinates.

In some embodiments relating to the method, the at least one beamformer parameter is selected from the group consisting of focus position, number of focal zones, receive filter frequency, and receive sampling frequency.

In some embodiments relating to the method, additional steps are included as follows: i) acquiring pre-scan raw ultrasound data frames based on the at least one adjusted beamformer parameter; ii) scan converting the pre-scan ultrasound data frames comprising the desired focal adjustment point to a post scan converted ultrasound image frame and iii) displaying the post scan converted ultrasound image frame with the desired focal adjustment point on the touchscreen display.

In some embodiments relating to the method, the ultrasound transducer is a curvilinear transducer.

In some embodiments relating to the method, the multi-purpose electronic device is communicatively coupled with the ultrasound transducer.

In some embodiments relating to the method, the touchscreen display shows a curvilinear ultrasound image feed, and the tap gesture on the touchscreen is at a location on or near an outer edge of the curvilinear ultrasound image feed.

In some embodiments relating to the method, the beamformer is adjusted based upon a distance (radial coordinate) and an angle (angular coordinate) of the polar co-ordinates.

In some embodiments relating to the method, more than one tap gesture is received on locations directly on the post scan converted ultrasound image frame, on the touchscreen display, such locations indicating more than one, sequential desired focal adjustment point, each defined by differing axial depths.

In some embodiments relating to the method, the tap gesture on the post scan converted ultrasound image frame, representing the desired focal adjustment point, is defined by pixels comprising a set of x, y coordinates on a cartesian space and the corresponding pre-scan raw ultrasound data frame is defined by a radial line and angle in a polar space ("polar coordinate"), and wherein the method comprises verifying bounds of the polar coordinate, ("verified bounds"); calculating depth based on sample inputs (wherein sample inputs=sampling rate÷speed of sound) of the verified bounds; calculating, using the depth, a new transmit focal point/aperture ("transmit beamformer"); acquiring new pre-scan raw ultrasound data frames based on the new transmit focal point/aperture; scan converting the new pre-scan ultrasound data frames comprising the new transmit focal point/aperture to a new post scan converted ultrasound image frame; and displaying the new post scan converted ultrasound image frame with the new transmit focal point/aperture on the touchscreen display.

In some embodiments relating to the method, the multi-purpose electronic device is selected from the group consisting of a smartphone, a tablet and a portable computer.

In a third broad aspect of the present disclosure, there is provided a computer readable medium storing instruction for execution by a processor communicatively coupled with a touchscreen display for an ultrasound imaging system, wherein when the instructions are executed by the processor, it is configured to show a touchscreen display on a multi-purpose electronic device, the touchscreen display comprising an ultrasound image feed with a post scan converted ultrasound image frame; receive a tap gesture at a location directly on the post scan converted ultrasound image frame on the touchscreen display, such location indicating a desired focal adjustment point, to modify the imaging depth of the ultrasound image feed; upon receipt of the tap gesture, revert the post scan converted ultrasound image frame comprising the location of the desired focal adjustment point, by way of cartesian co-ordinates, to its corresponding pre-scan raw ultrasound data frame; calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image frame.

D. Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging system, comprising:
a touchscreen display; and
a processor configured to execute instructions that cause the processor to provide a user interface on the touchscreen display, the user interface comprising an ultrasound image feed comprising a post scan converted ultrasound image frame;
wherein upon receipt of input of a tap gesture at a location on the touchscreen display, the location being away from a centre line of the post scan converted ultrasound image frame, and such location indicating on the post scan converted ultrasound image frame a desired focal adjustment point, the processor causes the ultrasound imaging system to:
revert the post scan converted ultrasound image frame comprising the location of the desired focal adjustment point, by way of the cartesian co-ordinates, to its corresponding pre-scan raw ultrasound data frame;
calculate, on the pre-scan raw ultrasound data frame, the location of the desired focal adjustment point, by way of polar coordinates of the desired focal adjustment point;
adjust at least one beamformer parameter of ultrasound signals being used to transmit and receive the ultrasound image to focus at the desired focal adjustment point, based upon the polar coordinates.

2. The ultrasound imaging system of claim 1 wherein the at least one beamformer parameter is selected from the group consisting of focus position, number of focal zones, receive filter frequency, and receive sampling frequency.

3. The ultrasound imaging system of claim 1, wherein the processor additionally causes the ultrasound system to: i) acquire additional pre-scan raw ultrasound data frames based on the at least one adjusted beamformer parameter; ii) scan convert the additional pre-scan ultrasound data frames comprising the desired focal adjustment point to an additional post scan converted ultrasound image frame; and iii) display the additional post scan converted ultrasound image frame with the desired focal adjustment point on the touchscreen display.

4. The ultrasound imaging system of claim 1 wherein the processor is communicatively coupled with a curvilinear ultrasound transducer.

5. The ultrasound imaging system of claim 4 wherein the touchscreen display shows a curvilinear ultrasound image feed, and a tap gesture on the touchscreen is at a location on or near an outer edge of the curvilinear ultrasound image feed.

6. The ultrasound imaging system of claim 1 wherein the beamformer is adjusted based upon a distance (radial coordinate) and an angle (angular coordinate) of the polar co-ordinates.

7. The ultrasound imaging system of claim 1 wherein the processor additionally causes the ultrasound system to respond to more than one tap gesture on locations on the touchscreen display, such locations indicating more than one, sequential desired focal adjustment point, each defined by differing axial depths.

8. The ultrasound imaging system of claim 1 wherein the entire ultrasound image feed on the touchscreen display is responsive to touch, to permit a user to input the tap gesture at any desired location for focal point adjustment.

9. The ultrasound imaging system of claim 1 wherein touchscreen display is part of a multi-purpose portable computing device.

10. A method for adjusting a focal point on an ultrasound image feed, acquired from an ultrasound transducer, the method comprising:
providing a touchscreen display on a multi-purpose electronic device, the touchscreen display showing the ultrasound image feed comprising a post scan converted ultrasound image frame;
receiving a tap gesture at a location on the touchscreen display, the location being away from a centre line of the post scan converted ultrasound image frame, and such location indicating a desired focal adjustment point, to modify the imaging depth of the ultrasound image feed;
upon receipt of the tap gesture,
revert the post scan converted ultrasound image frame comprising the location of the desired focal adjustment point, by way of cartesian co-ordinates, to its corresponding pre-scan raw ultrasound data frame;
calculate, on the pre-scan raw ultrasound data frame, the location of the desired focal adjustment point, by way of polar co-ordinates of the desired focal adjustment point; and
adjust at least one beamformer parameter of ultrasound signals being used to transmit and receive the ultrasound image frame to focus at the desired focal adjustment point, based upon the polar coordinates.

11. The method of claim 10 wherein the at least one beamformer parameter is selected from the group consisting of focus position, number of focal zones, receive filter frequency, and receive sampling frequency.

12. A method of claim 10 additionally including the steps of i) acquiring pre-scan raw ultrasound data frames based on the at least one adjusted beamformer parameter; ii) scan converting the pre-scan ultrasound data frames comprising the desired focal adjustment point to a post scan converted ultrasound image frame and iii) displaying the post scan converted ultrasound image frame with the desired focal adjustment point on the touchscreen display.

13. The method of claim 12, wherein the ultrasound transducer is a non-linear ultrasound transducer selected from the group consisting of curved transducers, curvilinear transducers, convex transducers, microconvex transducers, and endocavity transducers.

14. The method of claim 10, wherein the multi-purpose electronic device is communicatively coupled with the ultrasound transducer.

15. The method of claim 10 wherein the touchscreen display shows an ultrasound image feed which is non-linear, and the tap gesture on the touchscreen is at a location on or near an outer edge of the ultrasound image feed.

16. The method of claim 10 wherein the beamformer is adjusted based upon a distance (radial coordinate) and an angle (angular coordinate) of the polar co-ordinates.

17. The method of claim 10 wherein more than one tap gesture is received on locations on the touchscreen display, such locations indicating more than one, sequential desired focal adjustment point, each defined by differing axial depths.

18. The method of claim 10 wherein the tap gesture on the touchscreen display, representing the desired focal adjustment point, is defined by pixels comprising a set of x, y coordinates on a cartesian space ("cartesian coordinates") and the corresponding pre-scan raw ultrasound data frame is defined by a radial line and angle in a polar space ("polar coordinate"), and wherein the method comprises:
verifying bounds of the polar coordinate ("verified bounds");

calculating depth based on sample inputs (wherein sample inputs equals sampling rate plus speed of sound) of the verified bounds;

calculating, using the depth, a new transmit focal point/aperture ("transmit beamformer");

acquiring new pre-scan raw ultrasound data frames based on the new transmit focal point/aperture;

scan converting the new pre-scan ultrasound data frames comprising the new transmit focal point/aperture to a new post scan converted ultrasound image frame; and displaying the new post scan converted ultrasound image frame with the new transmit focal point/aperture on the touchscreen display.

19. The method of claim 10 wherein the multi-purpose electronic device is selected from the group consisting of a smartphone, a tablet and a portable computer.

20. A computer readable medium storing instruction for execution by a processor communicatively coupled with a touchscreen display for an ultrasound imaging system, wherein when the instructions are executed by the processor, it is configured to:

show a touchscreen display on a multi-purpose electronic device, the touchscreen display comprising an ultrasound image feed with a post scan converted ultrasound image frame;

receive a tap gesture at a location on the touchscreen display, the location being away from a centre line of the post scan converted ultrasound image frame, and such location indicating a desired focal adjustment point, to modify the imaging depth of the ultrasound image feed;

upon receipt of the tap gesture,
revert the post scan converted ultrasound image frame comprising the location of the desired focal adjustment point, by way of cartesian co-ordinates, to its corresponding pre-scan raw ultrasound data frame;

calculate, on the pre-scan raw ultrasound data frame, the location of the desired focal adjustment point, by way of polar co-ordinates of the desired focal adjustment point; and adjust at least one beamformer parameter of ultrasound signals being used to transmit and receive the ultrasound image frame to focus at the desired focal adjustment point, based upon the polar coordinates.

* * * * *